US005760089A

United States Patent [19]

Cronce

[11] Patent Number: 5,760,089

[45] Date of Patent: Jun. 2, 1998

[54] CHEMICAL WARFARE AGENT DECONTAMINANT SOLUTION USING QUATERNARY AMMONIUM COMPLEXES

[75] Inventor: Donald T. Cronce, Fredericksburg, Va.

[73] Assignee: The United States of America as represented by the Secretary of the Navy, Washington, D.C.

[21] Appl. No.: 615,348

[22] Filed: Mar. 13, 1996

[51] Int. Cl.$^{6}$ ........................ A01N 33/12; C07C 211/63; A62D 3/00

[52] U.S. Cl. ........................ 514/643; 564/643; 588/200

[58] Field of Search ........................ 564/282; 588/200; 514/643

[56] References Cited

U.S. PATENT DOCUMENTS

| | | | |
|---|---|---|---|
| 2,131,210 | 9/1938 | Baird et al. | 564/75 |
| 2,555,504 | 6/1951 | Nell | 514/643 |
| 3,620,807 | 11/1971 | Murray | 564/291 |
| 3,962,332 | 6/1976 | Trapasso | 564/204 |
| 4,022,911 | 5/1977 | Goldlaff et al. | 424/329 |
| 4,661,523 | 4/1987 | Disch et al. | 514/635 |
| 4,672,069 | 6/1987 | Sommer et al. | 514/346 |
| 4,672,122 | 6/1987 | Sommer et al. | 546/292 |
| 4,744,917 | 5/1988 | Scardera et al. | 252/187.28 |
| 4,784,699 | 11/1988 | Cowsar et al. | 134/42 |
| 4,798,870 | 1/1989 | Lyle, Jr. et al. | 525/327.1 |
| 4,850,729 | 7/1989 | Kramer et al. | 401/183 |
| 4,874,532 | 10/1989 | Worley | 210/755 |
| 4,914,132 | 4/1990 | Donofuo et al. | 514/643 |
| 5,010,183 | 4/1991 | Macfarlane | 536/27 |
| 5,019,173 | 5/1991 | Gettings et al. | 134/14 |
| 5,075,297 | 12/1991 | Dannard et al. | 514/183 |
| 5,116,512 | 5/1992 | Bartram et al. | 210/690 |
| 5,504,113 | 4/1996 | Lucero | 514/554 |

FOREIGN PATENT DOCUMENTS

| | | |
|---|---|---|
| 2041206 | 7/1992 | U.S.S.R. . |
| WO95/13122 | 5/1995 | WIPO . |

OTHER PUBLICATIONS

"Sulfonation and Sulfation to Thorium and Thorium Compounds", in Kirk-Othmer Encyclopedia of Chemical Technology, vol. 22, Third Edition, ed. John Wiley & Sons, Inc., pp. 383-385 (1983).

Y-C Yang et al., "Decontamination of Chemical Warfare Agents", *Chem. Rev.,* 92(8):1729-1743 (1992).

*Primary Examiner*—Deborah Lambkin

*Attorney, Agent, or Firm*—James B. Bechtel, Esq.

[57] ABSTRACT

A chemical warfare agent decontamination solution made up of about 30-45% of a quaternary ammonium complex containing benzyltrimethylammonium chloride and benzyltriethylammonium chloride dissolved in a solvent, such as water or glycol, is provided. This solution is a noncorrosive, nontoxic, nonflammable decontaminant, which may also be used to neutralize organophosphorus agricultural chemicals.

20 Claims, No Drawings

CHEMICAL WARFARE AGENT DECONTAMINANT SOLUTION USING QUATERNARY AMMONIUM COMPLEXES

FIELD OF THE INVENTION

This invention relates generally to the field of compositions useful in decontamination of material, equipment and personnel exposed to chemical warfare agents.

BACKGROUND OF THE INVENTION

Methods for decontamination of chemical warfare agents, which include a variety of organophosphorus and organosulfur compounds, are known in the art. However, these known methods use compositions which have certain undesirable properties, including corrosiveness, flammability and toxicity. For example, hypochlorite formulations are very corrosive and toxic. Additionally, many decontaminants degrade upon exposure to water and carbon dioxide, requiring that these solutions be prepared and used the same day they are needed. Further, application of the hypochlorite decontaminant often requires substantial scrubbing for removal and destruction of the chemical warfare agent, a procedure which limits its use.

One decontaminant, Decontamination Solution 2 (DS2), is useful against a variety of agents and contains 70% diethylenetriamine, 28% ethylene glycol monomethyl ether and 2% sodium hydroxide. However, DS2 will spontaneously ignite upon contact with hypochlorites and hypochlorite-based decontaminants. Further, DS2 may cause corrosion to aluminum, cadmium, tin, and zinc after prolonged contact, and softens and removes paint.

A need exists for a chemical warfare agent decontamination solution which is noncorrosive, nontoxic, nonflammable, and environmentally safe.

SUMMARY OF THE INVENTION

The invention provides a chemical warfare agent decontamination composition comprising about 30 to about 45%, by weight, of a quaternary ammonium complex in a nontoxic, non-flammable solvent. Depending on the solvent selected, the decontaminant of the invention may optionally contain corrosion inhibitors, buffers, catalysts and the like. Advantageously, this composition is nontoxic, noncorrosive and non-flammable.

In a preferred embodiment, the quaternary ammonium complex consists of a mixture of benzyltrimethylammonium chloride and benzyltriethylammonium chloride and the solvent is water. The corrosion inhibitor is 2-amino-2-methyl-1-propanol. In an alternative embodiment, the solvent is a diol.

In another aspect, the invention provides a method for decontaminating chemical warfare agents comprising applying a chemical warfare agent decontaminant as described herein to a contaminated surface.

Other aspects and advantages of the present invention are described further in the following detailed description of the preferred embodiments thereof.

DETAILED DESCRIPTION OF THE INVENTION

The present invention provides a chemical warfare agent decontamination formulation containing a quaternary ammonium complex (QAC) solvated in a non-corrosive, non-toxic and non-flammable solution. The decontaminant of the invention is non-flammable and does not degrade significantly over time after exposure to atmospheric carbon dioxide and water. Advantageously, the reaction of the decontaminant of the invention with chemical warfare agents occurs very rapidly.

The decontaminant of the invention contains between about 30% to about 45%, by weight, of a QAC. As defined herein, a QAC has the general structure provided below.

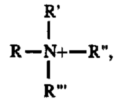

where R, R', R", and R'" are any alkyl or aryl organic species capable of chemically bonding to the nitrogen atom, N, through a carbon atom. Preferred QAC for use in preparing the decontaminant of the invention are the chloride salts of benzyltriethylammonium (R is benzyl and R', R", and R'" are $-CH_2CH_3$) and benzyltrimethylammonium (R is benzyl and R', R"and R'" are $-CH_3$). In a preferred embodiment, the decontaminant of the invention contains a mixture of benzyltriethylammonium chloride and benzyltrimethylammonium chloride. Desirably, the benzyltrimethylammonium chloride makes up between about 25% to about 35%, by weight of the decontaminant solution and the benzyltriethylammonium chloride makes up about 5% to about 10%, by weight of the decontaminant solution. Alternatively, one of skill in the art may readily substitute other appropriate salts for the chloride salt of the QAC. Particularly preferred salts include the hydroxide salts.

The selected QAC is mixed with a suitable non-flammable, non-corrosive, nontoxic solvent. Preferably, this solvent is water, which is present in an amount between about 10% to about 15%, by weight, of the decontaminant. In another embodiment, the solvent is a diol. One particularly desirable diol is 1,2-propanediol (propylene glycol). However, other diols capable of solvating both polar and low-polarity compounds may be readily substituted. For example, suitable diols may include other 1,2-alkanediols, particularly where the alkane is butane, pentane or hexane. Where the solvent used is propylene glycol, it is preferably present in an amount of about 45%, by weight, of the composition, i.e., roughly equivalent to the weight percentage of the QAC present in the composition.

The based decontaminant of the invention may contain a corrosion inhibitor. Suitable corrosion inhibitors include amino alcohols, such as 2-amino-2- methyl-1-propanol. One of skill in the art may substitute other non-toxic corrosion inhibitors, which may be selected from among primary amines and polyamines.

When the decontaminant of the invention is water-based, as described herein, a corrosion inhibitor is required and may also be used as a solvent. In such a formulation, the corrosion inhibitor may be found in an amount up to about 55%, by weight, of the decontaminant. Alternatively, when the solvent is a diol, the corrosion inhibitor may make up less than about 10%, by weight, of the decontaminant formulation.

The decontaminant of the invention may optionally contain preservatives, buffers, and reaction catalysts. Such components, and the required amounts thereof, are well known and can be readily selected by one of skill in the art. See, e.g, Yang, et al., *Chem. Rev.*, 92(8):1729 (1992).

Two particularly preferred decontaminant formulations of the invention are provided below. The approximate weight percentages of the components of the formulations are provided in columns A and B, respectively. Column 2 identifies the number of the component by reference to its accession number in Chemical Abstracts Service.

TABLE 1

| Component | CAS Number | A Weight Percent | B Weight Percent |
|---|---|---|---|
| Benzyltrimethyl ammonium chloride | 56-93-9 | 35 | 25–30 |
| Benzyltriethyl ammonium chloride | 56-37-1 | 10 | 5–10 |
| 2-amino-2-methyl-1-propanol | 124-68-5 | 0–10 | 50–55 |
| Sodium perborate tetrahydrate | 10486-00-7 | 2–10 | 2–10 |
| 1,2-propanediol (propylene glycol) | 57-55-6 | 45 | — |
| Water | 7732-18-5 | — | 10–15 |

Advantageously, a diol-based decontaminant of the invention, stored under ambient conditions, showed no changes in its infrared spectrum over a period of six weeks, with the exception of an absorption of atmospheric water. A water-based decontaminant of the invention also appeared unchanged for at least one week, when exposed to a range of temperatures of 5° F. to 115° F. These tests indicate that the formulations are stable with respect to atmospheric exposure. Further, none of the components used in these compositions are listed as flammable or corrosive in the *OSHA Regulated Hazardous Substances: Health, Toxicity, Economic and Technological Data*, Occupational Safety and Health Administration of the U.S. Department of Labor, Noyes Data Corporation (Park Ridge, N.J., 1990).

Thus, the decontaminant compositions of the invention are believed to be stable, nontoxic and useful in detoxifying/neutralizing a variety of chemical warfare agents, including organosulfur agents such as mustard gas (HD), and organophosphorus agents such as the nerve agents termed VX and GD. The decontaminants of the invention may also be used to neutralize selected organophosphorus agricultural chemicals. Decontamination is effected by applying a decontaminant of the invention to the contaminated material, equipment, personnel, or the like. Such application may be spraying, showering, washing or other suitable means.

The amount of decontaminant required under field conditions can be readily determined by one of skill in the art. The decontaminant is typically used in a ratio approaching or exceeding at least about 100:1 decontaminant:chemical agent. However, it has been tested under laboratory conditions at a much lower ratio of decontaminant to agent (about 10:1). See, Examples 2 and 3.

These examples illustrate the preferred methods for preparing and applying the decontaminant of the invention. These examples are illustrative only and do not limit the scope of the invention.

EXAMPLE 1

Decontamination Formulations

A. Diol-Based Formulation

Because of their hygroscopic natures, benzyltrimethylammonium chloride (55 g) and benzyltriethylammonium chloride (15 g) were oven dried before use. Along with sodium perborate tetrahydrate (2 g), they were then added to a heated (about 45° C.) mixture of propylene glycol (68 g) and 2-amino-2-methyl-1-propanol (12 g). The propylene glycol-2-amino-2-methyl-1-propanol solution was heated to aid the dissolution of the sodium perborate tetrahydrate without it decomposing (sodium perborate tetrahydrate decomposes at about 60° C.). The final mixture was stirred until the solid components have substantially dissolved. The mixtures were removed from the stirring and allowed to remain undisturbed. More solid dissolved while undissolved solids settled out of solution. When no more solid dissolved, the solution was decanted then stored in a sealed container. The decanted solution was clear with a golden color.

This formulation was used in the neutralization studies in Example 2 below.

B. Water-Based Decontaminant Formulation

Benzyltrimethylammonium chloride (90 g) and benzyltriethylammonium chloride (25 g) were oven dried before use. They were added to a heated solution of 2-amino-2-methyl-1-propanol (185 g) and water (20 g). Sodium perborate tetrahydrate (2 g) was then added. This solution was treated similarly to the QAC/glycol solution described in Example 1A. The pH of the decanted solution was adjusted to about 10.6 (about 20 g water was added).

This formulation was used in the neutralization studies described in Example 3 below.

EXAMPLE 2

Neutralization of Chemical Warfare Agents

The following results illustrate the neutralization of mustard gas (HD) and two nerve agents using the diol-based decontaminant formulated as described in Example 1A above and at a ratio of about 10:1 decontaminant:agent.

A. HD Neutralization Assay

The neutralization reactions were conducted under ambient conditions as follows. 150 mg of HD (sulfur mustard, CAS Registry No. 505-60-2) in a 13×100 mm culture tube was immediately Vortex mixed upon addition of 1.0 mL decontaminant. A 0.025 mL aliquot of the mixture was immediately withdrawn, and then added to and mixed with 1.0 mL n-butanol to quench the reaction. Serial dilutions, using n-butanol, were made to bring the concentration of the quenched reaction mixture into the analytical range of the DB-3 colorimetric analytical method (0.5–20 micrograms HD). Additional 0.025 mL aliquots of the original mixture were withdrawn after specified time periods, and treated and analyzed in the manner just described. The DB-3 method determined the amount of unneutralized HD; using the DB-3 result and the amount of HD originally present in the 0.025 mL aliquot, the percent neutralization was calculated.

The DB-3 method was performed as follows. The DB-3 concentrate was prepared by mixing equal volumes of a solution of 336 mg/mL sodium perchlorate in distilled water and a solution of 24 mg/mL 4-(p-nitrobenzyl pyridine) in methyl cellosolve. The pH of the concentrate was adjusted to 6.5–7.5 with concentrated 3-(n-morpholino)-propane sulfonic acid (MOPS) and the concentrate was refrigerated. 1.0 mL of the final n-butanol solution described earlier was mixed with 1.0 mL diethyl phthalate and 1.0 mL DB-3 concentrate and shaken vigorously. The solution was heated 15 minutes in boiling water bath, then cooled in a room temperature water bath. Immediately following the addition of 0.5 mL diethylamine, the absorbance was measured at 575 nm. The intensity of the resulting purple color is directly proportional to the amount of HD present in solution.

The results are provided below.

| Time (min) | % Neutralization |
|---|---|
| 0–2 | 2 |
| 3 | 5 |

-continued

| Time (min) | % Neutralization |
|---|---|
| 10 | 7 |
| 30 | 7 |
| 60 | 8 |

B. Neutralization of VX

The neutralization reactions were conducted under ambient conditions. 0.1 mL of VX (CAS Registry No. 50782-69-9) in a 13×100 mm culture tube was immediately Vortex mixed upon addition of 1.0 mL decontaminant. A 0.025 mL aliquot of the mixture was immediately withdrawn, and then added to and mixed with 4.97 mL 0.2M sodium dihydrogen phosphate to quench the reaction. Serial dilutions, using deionized water, were made to bring the concentration of the quenched reaction mixture into the analytical range of the acetylcholinesterase inhibition method (0.0002 micrograms). Additional 0.025 mL aliquots of the original mixture were withdrawn after specified time periods, and treated and analyzed in the manner just described. The acetylcholinesterase inhibition method determines the rate of change of the acetylcholinesterase enzyme activity; the rate of change of the enzyme activity, determined spectroscopically, is directly related to the amount of VX present in the 0.025 mL aliquot. Using this result with the amount of VX originally present in the aliquot, the percent neutralization was determined by an acetylcholinesterase inhibition method performed as follows. However, other assays may be used. Several diagnostic kits are commercially available (e.g., through Sigma Chemical Corporation of St. Louis, Mo.).

The method used in these analyses involved several stock solutions. A buffer concentrate consisting of 18.2 g tris-(hydroxymethyl) aminomethane and 31.4 g MOPS in 100 mL water at pH=7.8 was prepared. An enzyme stock (refrigerated) was prepared by adding a small, unmeasured quantity of lyophilized enzyme in 10 mL water containing 0.3 mL of the buffer concentrate and 100 mg bovine serum albumin. An enzyme working solution (refrigerated) was prepared by diluting the enzyme stock solution (with the buffer/albumin solution) to produce a 0.5–0.6 change in absorbance in 1 minute at 412 nm. A substrate concentrate (refrigerated) contained 200 mg acetylthiocholine iodide in 10 mL water. Finally, a DTNB solution (refrigerated) was made by dissolving 40 mg 5,5'-dithiobis-(2-nitrobenzoic acid) in 0.6 mL buffer concentrate and diluted with water to 20 mL, and then adding 350 mg calcium chloride and 640 mg magnesium chloride hexahydrate.

To determine the activity inhibition of the test sample, 0.1 mL of buffer concentrate and 0.005 mL enzyme working solution was added to 2.0 mL water. The sample was then incubated for 6 minutes in a 30° C. water bath. Following addition of 1.0 mL of the test sample and mixing, the sample was incubated for an additional 10 minutes. Finally, 0.1 mL DTNB and 0.05 mL substrate solutions were added. Immediately following mixing, the absorbance change was measured at 412 nm for 1 minute.

| Time (min) | % Neutralization |
|---|---|
| 0–2 | 1 |
| 3 | 4 |
| 10 | 7 |
| 30 | 8 |
| 60 | 8 |

C. Neutralization of GD

The neutralization reactions were performed as described in part B. above substituting GD (soman, CAS Registry No. 96-64-0) for VX. The results are provided below.

| Time (min) | % Neutralization |
|---|---|
| 0–2 | 5 |
| 3 | 12 |
| 10 | 30 |
| 30 | 66 |
| 60 | 84 |

The results in A.–C. indicate that a diol-based decontaminant of the invention will provide adequate neutralization when used at a ratio achievable under field conditions.

EXAMPLE 3

Neutralization of Chemical Warfare Agents

The following results illustrate the neutralization of mustard gas (HD) and two nerve agents using the decontaminant formulated as described in Example 1B above.

A. Neutralization of HD

Test conditions were as described above in Example 1A, except the decontaminant/HD w/w ratio was (20:1), twice the value in Example 2A.

| Time (min) | % Neutralization |
|---|---|
| 0–1 | 52 |
| 10 | 53 |
| 30 | (47)* |
| 60 | 61 |

B. Neutralization of VX

Test conditions were as described above in Example 2B.

| Time (min) | % Neutralization |
|---|---|
| 0–1 | 5 |
| 10 | 11 |
| 30 | 20 |
| 60 | 27 |
| 120 | 36 |

C. Neutralization of GD

Test conditions were as described above in Example 2C.

| Time (min) | % Neutralization |
|---|---|
| 0–1 | 23 |
| 10 | 92 |
| 30 | >99 |
| 60 | >99 |

The results in A.–C. indicate that a water-based decontaminant of the invention will provide neutralization when used at a ratio typically found in field conditions, about 100:1 decontaminant:agent.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A chemical warfare agent decontamination composition comprising a non-toxic, non-flammable solvent and 30 to 45%, by weight, of a quaternary ammonium complex, wherein the quaternary ammonium complex consists of a mixture of benzyltrimethylammonium chloride and benzyltriethylammonium chloride.

2. The composition according to claim 1, wherein the benzyltrimethylammonium chloride is about 25% to 30%, by weight, of the composition and the benzyltriethylammonium chloride is about 5 to 10%, by weight of the composition.

3. The composition according to claim 2, wherein the benzyltrimethylammonium chloride is about 35%, by weight, of the composition and the benzyltriethylammonium chloride is about 10%, by weight of the composition.

4. The composition according to claim 1, wherein the solvent is water.

5. The composition according to claim 4, wherein the solvent is about 10 to 15%, by weight, of the composition.

6. The composition according to claim 1, wherein the solvent is a diol.

7. The composition according to claim 6, wherein the diol is selected from the group consisting of propylene glycol, 1,2-butanediol, 1,2-pentanediol, and 1,2-hexanediol.

8. The composition according to claim 6 wherein the diol is about 45%, by weight, of the composition.

9. The composition according to claim 1 further comprising a corrosion inhibitor.

10. The composition according to claim 9, wherein the corrosion inhibitor is selected from the group consisting of an amino alcohol, an amine or a polyamine.

11. The composition according to claim 1 wherein said composition further comprises a buffer, a reaction catalyst or a preservative.

12. A chemical warfare agent decontamination solution consisting essentially of:

about 25 to 35%, by weight, of benzyltrimethylammonium chloride;

about 5 to 10%, by weight, benzyltriethylammonium chloride;

less than about 55%, by weight, 2-amino-2-methyl-1-propanol;

less than about 1%, by weight, sodium perborate tetrahydrate; and about 10 to 15%, by weight, water.

13. A chemical warfare agent decontamination composition consisting essentially of:

about 35%, by weight, benzyltrimethylammonium chloride;

about 10%, by weight, benzyltriethylammonium chloride; and about 45%, by weight, propylene glycol;

less than about 10%, by weight, 2-amino-2-methyl-1-propanol; and less than about 2%, by weight sodium perborate tetrahydrate.

14. A method for decontaminating chemical warfare agents comprising applying to a contaminated surface a chemical warfare agent decontamination composition comprising a non-toxic, non-flammable solvent and 30 to 45%, by weight, of a quaternary ammonium complex, wherein the quaternary ammonium complex consists of a mixture of benzyltrimethylammonium chloride and benzyltriethylammonium chloride.

15. The method according to claim 14, wherein the benzyltrimethylammonium chloride consists of about 25% to 30%, by weight, of the composition and the benzyltriethylammonium chloride consists of about 5 to 10%, by weight of the composition.

16. The method according to claim 15, wherein the benzyltrimethylammonium chloride consists of about 35%, by weight, of the composition and the benzyltriethylammonium chloride consists of about 10%, by weight of the composition.

17. The method according to claim 14 wherein the solvent is selected from the group consisting of water, propylene glycol, 1,2-butanediol, 1,2-pentanediol, and 1,2-hexanediol.

18. The method according to claim 17 wherein the propylene glycol is about 45%, by weight, of the composition.

19. The method according to claim 17, wherein the solvent is water and the composition further comprises a corrosion inhibitor selected from the group consisting of an amino alcohol, an amine or a polyamine.

20. The method according to claim 19, wherein the solvent is about 10 to 15%, by weight, of the composition.

* * * * *